(12) United States Patent
Aliski et al.

(10) Patent No.: US 7,507,218 B2
(45) Date of Patent: Mar. 24, 2009

(54) STENT WITH FLEXIBLE ELEMENTS

(75) Inventors: Peter Aliski, Newton, MA (US); Vasu Nishtala, Snellville, GA (US); Benedict Shia, Needham, MA (US); Anthony Tremaglio, Charlestown, MA (US)

(73) Assignee: Gyrus Acmi, Inc., Southborough, MA (US)

( * ) Notice: Subject to any disclaimer, the term of this patent is extended or adjusted under 35 U.S.C. 154(b) by 542 days.

(21) Appl. No.: 10/832,859

(22) Filed: Apr. 26, 2004

(65) Prior Publication Data
US 2005/0240277 A1 Oct. 27, 2005

(51) Int. Cl.
*A61F 2/04* (2006.01)
*A61M 5/00* (2006.01)

(52) U.S. Cl. .................. 604/8; 623/23.66; 623/23.7
(58) Field of Classification Search ............. 623/2.37, 623/23.66, 23.7; 604/8
See application file for complete search history.

(56) References Cited

U.S. PATENT DOCUMENTS

| | | |
|---|---|---|
| 3,397,699 A | 8/1968 | Kohl |
| 3,938,529 A | 2/1976 | Gibbons |
| 4,531,933 A | 7/1985 | Norton et al. |
| 4,610,657 A | 9/1986 | Densow |
| 4,671,795 A | 6/1987 | Mulchin |
| 4,813,925 A | 3/1989 | Anderson, Jr. et al. |
| 4,874,360 A * | 10/1989 | Goldberg et al. ............. 604/8 |
| 4,950,228 A | 8/1990 | Knapp |
| 5,073,166 A | 12/1991 | Parks et al. |
| 5,167,239 A | 12/1992 | Cohen et al. |
| 5,176,625 A | 1/1993 | Brisson |
| 5,176,626 A | 1/1993 | Soehendra |
| 5,282,860 A | 2/1994 | Matsuno et al. |
| 5,354,263 A | 10/1994 | Coll |
| 5,380,270 A * | 1/1995 | Ahmadzadeh ............. 604/9 |
| 5,518,498 A | 5/1996 | Lindenberg et al. |
| 5,554,189 A | 9/1996 | De La Torre et al. |
| 5,599,291 A | 2/1997 | Balblerz et al. |
| 5,662,713 A | 9/1997 | Andersen et al. |
| 5,681,274 A | 10/1997 | Perkins et al. |

(Continued)

FOREIGN PATENT DOCUMENTS

DE 69510973 3/2000

(Continued)

OTHER PUBLICATIONS

German Patent Office Examination Report dated Jul. 26, 2006 for German serial No. 102004047954.2, filed Oct. 1, 2004, 4pps. [Source for cited references only—No English translation provided to Applicant. and therefore relevance is not known.

(Continued)

*Primary Examiner*—Thomas J Sweet

(57) ABSTRACT

In accordance with the invention, there are provided medical devices for providing a fluid passage between two areas in the body. An embodiment of the present invention relates to a stent comprising a tubular member comprising a distal transition region and a proximal transition region adapted to provide the ability for the stent to accommodate the dynamic urinary tract anatomy that stretches and relaxes. The distal transition region and the proximal transition region is adapted to exhibit a physical property that provides both longitudinal elasticity, allowing for stretch and recoil, as well as radial elasticity, allowing for bending and recovery.

10 Claims, 4 Drawing Sheets

U.S. PATENT DOCUMENTS

| | | |
|---|---|---|
| 5,766,209 A | 6/1998 | Devonec |
| 5,795,319 A | 8/1998 | Ali |
| 5,876,445 A | 3/1999 | Andersen et al. |
| 5,916,195 A | 6/1999 | Eshel et al. |
| 5,964,744 A | 10/1999 | Balbierz et al. |
| 6,146,416 A | 11/2000 | Andersen et al. |
| 6,214,036 B1 | 4/2001 | Letendre et al. |
| 6,258,117 B1 * | 7/2001 | Camrud et al. ............. 623/1.16 |
| 6,267,783 B1 | 7/2001 | Letendre et al. |
| 6,305,436 B1 | 10/2001 | Andersen et al. |
| 6,350,252 B2 | 2/2002 | Ray et al. |
| 6,355,070 B1 | 3/2002 | Andersen et al. |
| 6,368,356 B1 | 4/2002 | Zhong et al. |
| 6,395,021 B1 | 5/2002 | Hart et al. |
| 6,505,654 B1 | 1/2003 | Andersen et al. |
| 6,582,472 B2 | 6/2003 | Hart |
| 6,656,146 B1 | 12/2003 | Clayman et al. |
| 6,676,623 B2 | 1/2004 | Whitmore, III |
| 6,685,744 B2 | 2/2004 | Gellman et al. |
| 6,709,465 B2 | 3/2004 | Mitchell et al. |
| 6,764,519 B2 * | 7/2004 | Whitmore, III ............ 623/23.7 |
| 6,887,215 B2 | 5/2005 | McWeeney |
| 6,908,447 B2 | 6/2005 | McWeeney et al. |
| 6,913,625 B2 | 7/2005 | Segura et al. |
| 6,929,663 B2 | 8/2005 | Rioux et al. |
| 6,949,125 B2 | 9/2005 | Robertson |
| 7,041,139 B2 | 5/2006 | Bluni et al. |
| 2001/0053936 A1 | 12/2001 | Whitmore, III |
| 2002/0183852 A1 | 12/2002 | McWeeney |
| 2003/0018291 A1 | 1/2003 | Hill et al. |
| 2003/0040803 A1 | 2/2003 | Rioux et al. |
| 2003/0163204 A1 | 8/2003 | Rix |
| 2003/0176831 A1 * | 9/2003 | Gellman et al. ................ 604/8 |
| 2004/0059279 A1 | 3/2004 | McWeeney et al. |
| 2004/0087886 A1 | 5/2004 | Gellman |
| 2005/0165366 A1 | 7/2005 | Brustad et al. |
| 2005/0187510 A1 | 8/2005 | McWeeney |
| 2005/0240141 A1 | 10/2005 | Aliski et al. |
| 2005/0240278 A1 | 10/2005 | Aliski et al. |
| 2005/0240280 A1 | 10/2005 | Aliski et al. |
| 2006/0015190 A1 | 1/2006 | Robertson |

FOREIGN PATENT DOCUMENTS

| | | |
|---|---|---|
| DE | 10155767 | 5/2003 |
| EP | 00365269 | 4/1990 |
| EP | 00516189 | 12/1992 |
| EP | 0593948 | 4/1994 |
| EP | 0672394 | 7/1999 |
| EP | 1214917 | 6/2002 |
| JP | 10234858 | 9/1998 |
| WO | WO93/21985 A1 | 4/1993 |
| WO | WO94/12136 | 6/1994 |
| WO | WO96/11721 | 4/1996 |
| WO | WO96/30070 | 10/1996 |
| WO | WO99/04724 | 2/1999 |
| WO | WO99/32051 A1 | 7/1999 |
| WO | WO00/50116 A1 | 8/2000 |
| WO | WO0062708 A1 | 10/2000 |
| WO | WO/02/098500 | 12/2002 |
| WO | WO02/098500 A1 | 12/2002 |
| WO | WO03/030981 | 4/2003 |
| WO | WO03/075795 | 9/2003 |
| WO | WO03/079930 | 10/2003 |
| WO | WO03/079934 | 10/2003 |
| WO | WO03/089038 | 10/2003 |
| WO | WO2004/041345 A1 | 5/2004 |

OTHER PUBLICATIONS

Circon 1999-2000 Complete Product Catalog, Circon Surgitek, Ureteral Stents, Catalog pp. U-107 to U-132, Circon Corporation.

* cited by examiner

STENT WITH FLEXIBLE ELEMENTS

FIELD OF THE INVENTION

The present invention is related to ureteral stents, and more particularly, to methods and apparatus for stent shaft improvement.

BACKGROUND

Tubular prostheses, commonly called stents, are used in a variety of medical procedures. For example, stents are often used in connection with assisting drainage from the kidney through the ureter, from the liver through the biliary ducts, from the dorsal or ventral pancreas through the pancreatic ducts, from the gall bladder through the cystic, hepatic, or common bile ducts, and the like. A leading reason for stent deployment in ducts is to provide drainage to circumvent a blockage. Blockage of ducts in the body can be a serious and very painful affliction that can result in death if not promptly and effectively treated. Blockages can occur for a number of reasons. For example, stones or debris from such stones can pass from into the ureter, where they become entrapped. Similarly, stones or debris can pass from the gall bladder into the bile ducts, where they become entrapped. Alternatively, cysts or tumors growing against the outer wall of the ducts can cause constriction of the ducts. Similarly, internal or duct wall cysts or tumors can act to block ducts.

The main function ureteral stents, for example, is to bypass ureteral obstruction and to provide urinary drainage from the kidney to the bladder for a period of time, typically a few days to several months. The ureteral stent is usually provided with drainage means such as a lumen for directing fluid from the renal pelvis to the bladder. Conventional stents include openings provided along the stent for communication with the lumen to aide in drainage.

Early ureteral stents were straight. As a result, after placement into the ureter, these straight stents often migrated or were expelled from the ureter as a result of peristaltic action by the ureter. Later ureteral stents, therefore, were usually designed with means of retention on one or both ends of the stent. The retention means is intended to inhibit stent migration either upward into the kidney or downward into the bladder. Retention means that have been employed are in the form of hooks, pigtails, coils, corkscrews, malecots, barbs, mushrooms, or any other practical shape that serves the purpose.

Current urinary stents comprise a shaft commonly made of either single or dual durometer polymer material. Current shaft designs often have unique profile cross-sections and hydrophilic or anti-microbial coatings, for example. This shaft typically resides in the ureter to provide drainage of urine after ureteroscopy procedures. Anecdotally, it is believed that the softer the material, the less irritation to the ureter, and the greater the patient comfort. The problem with making the shaft extremely soft is its lack of stiffness makes it difficult to insert it into the patient. Hence for placement, a certain axial stiffness is built in which equates to a high level of radial stiffness. Stiff stents are believed to be felt by the muscle spasm of the ureter, potentially causing patient discomfort. Further, the axial stiffness of current stents may not be ideal for comfort to the urinary tract anatomy without being felt by the patent.

In addition to varying lengths, ureteral stents are also made with varying diameters, e.g., from 3 French (1 mm) to 16 French (5.28 mm), and typically, 4.5 French (1.5 mm) to 8.5 French (2.8 mm), and varying degrees of hardness. Ureteral stents with smaller diameters are usually easier to insert but may provide insufficient drainage, whereas stents with larger diameters allow for increasing drainage capacity through the ureter but may be difficult to insert. Stiff ureteral stents are also easier to insert than are softer stents, but once inserted can lead to increased patient discomfort. Stiff stents are less likely to accommodate the dynamic urinary tract anatomy that stretches and relaxes. Stiff stents do not accommodate the relative push-and-pull of the kidney and bladder, increasing patient discomfort from contact irritation of the stent within the anatomy. In addition, the lack of accommodation of the normal body movements increases the potential for the stent to migrate or dislodge from its intended location.

Softer stents, on the other hand, provide more comfort for the patient but are more difficult to insert due to their softness. Presently, most available stents are made of either silicone or of a harder polymer. Silicone may increase patient comfort, but because of the softness of silicone, it is more difficult to guide the stent into the ureter. Once in the ureter, the softness of the silicone increases the likelihood of migration of the stent because rigid retention means are not available.

Thus, although stents have been designed to address one or more of the above problems specifically, there are currently no devices incorporating features that can be used to bypass most of the aforementioned disadvantages. It would thus be desirable to have a stent that provides one or more of the following attributes, easy insertion or implantation, strong retention, and increased patient comfort.

BRIEF DESCRIPTION OF THE DRAWINGS

Like reference numbers indicate corresponding elements in the figures.

SUMMARY OF THE INVENTION

Figure 1:
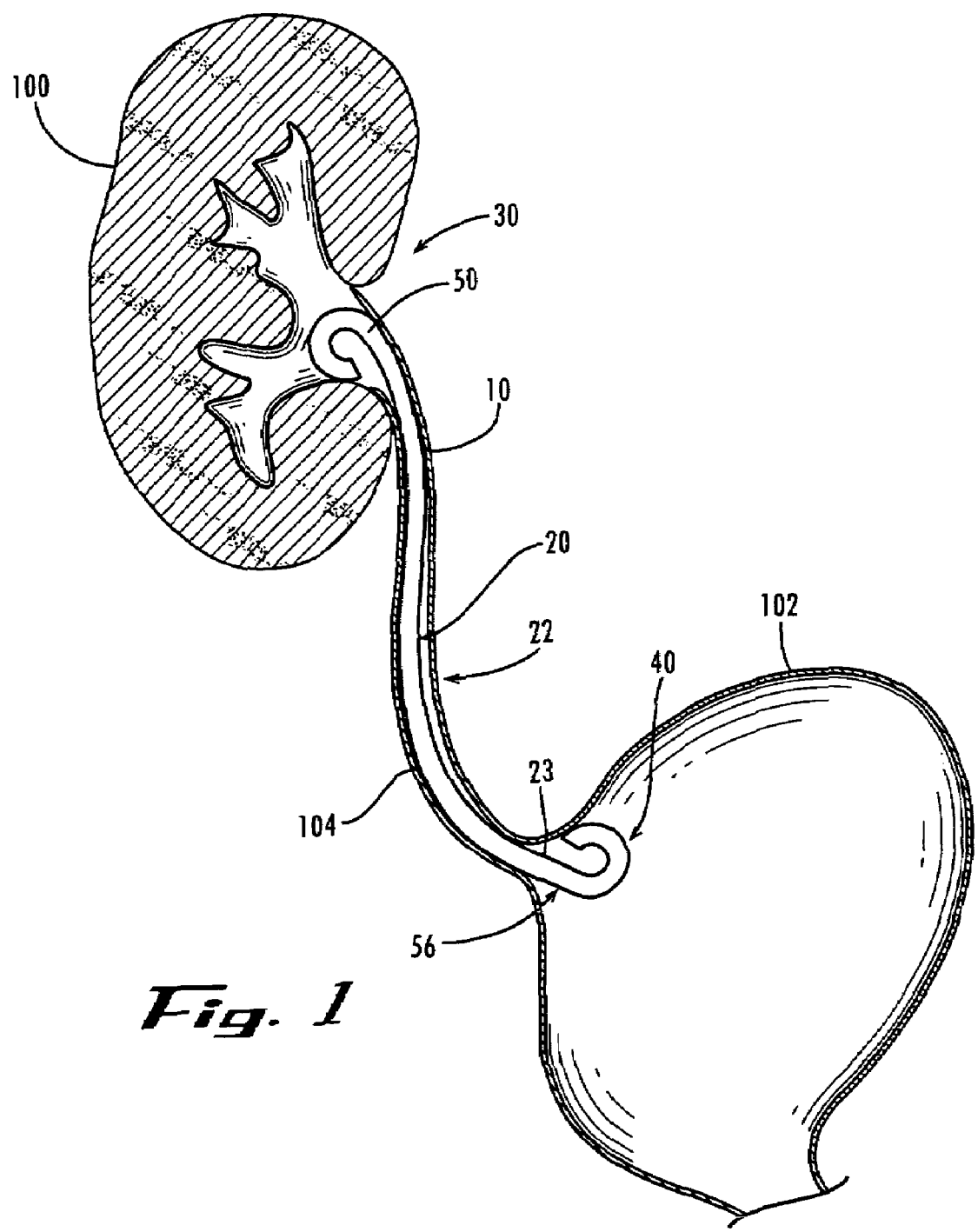
FIG. 1 is a front partial cross-sectional view of a ureteral stent within anatomy in accordance with an embodiment of the present invention.

The present invention provide embodiments of medical devices that provide for fluid drainage while maintaining patient comfort.

An embodiment of the present invention relates to a stent comprising a tubular member having a body portion, a proximate end portion, and a distal end portion, the tubular member having an axial lumen therein adapted to provide fluid communication from the distal end portion to the proximal end portion, the tubular member further comprising a resilient distal transition region coupling the distal end portion to the body portion. One advantage of this embodiment of the invention is, for example, that the resilient distal transition region increases patient comfort by providing enhanced flexibility to accommodate the bending and stretching of the anatomy. A second advantage of this embodiment of the invention is, for example, that the resilient distal transition region improves stent retention within the anatomy.

In accordance with other embodiments, the distal and proximal transition regions comprise a material exhibiting a physical property that provides both longitudinal elasticity allowing for stretch and recoil as well as radial elasticity allowing for bending and recovery. Another embodiment provides a resilient distal transition region characterized as a region comprising a more-compliant material than that comprising the body portion and/or the distal end portion. A further embodiment provides a body portion comprising a wall having a first wall thickness, the resilient distal transition region having a wall with a second wall thickness less than the first wall thickness. Another embodiment provides a resilient distal transition region comprising a resilient coupling member adapted to couple the body portion to the distal end portion.

In accordance with another embodiment of the present invention, the stent comprises an elongated member having a body portion, a proximate end portion, and a distal end portion. The elongated member is formed into a helical coil defining an axial lumen therein adapted to provide fluid communication from the distal end portion to the proximal end portion. The elongated member comprises a resilient material. In one embodiment, the elongated member comprises a material exhibiting shape-memory properties wherein the elongated member tends to return to a predetermined configuration when stretched or otherwise deformed. In another embodiment, the stent further comprises a structural member coupled to and along substantially the length of the body portion, the structural member adapted to impart and resiliently retain a predetermined configuration to the body portion when stretched or otherwise deformed. In yet another embodiment, the distal end portion further comprises a guidewire-coupling fixture adapted to removably couple with an end of a guidewire, providing a means for the guidewire to push the distal end portion into anatomy.

DETAILED DESCRIPTION

Reference will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

The invention relates to embodiments of medical devices (e.g., stents) for draining fluids. The invention increases patient comfort and prevents fluid retention if a stricture in a vessel develops. For simplicity and illustration, embodiments of the invention are described herein in the context of draining urine from a kidney, through a ureter, and into the bladder. However, the invention is applicable to any situation that requires drainage within a body, from a body, or from one body structure to another. One such situation is, for example, biliary drainage from the gall bladder, through the biliary ducts, to the duodenum.

FIG. 1 is a front partial cross-sectional view of a ureteral stent 10 within anatomy in accordance with an embodiment of the present invention. The stent 10 comprises an elongated tubular member 20 having a relatively straight body portion 22 and opposed distal end portion 30 and proximal end portion 40. The distal end portion 30 is provided with a shape for retaining the distal end portion 30 in a kidney 100 and a shape for retaining the proximal end portion 40 in a bladder 102. The proximal end portion 40 of the stent 10 may have any of a variety of configurations providing a desired retaining effect, or it may be entirely straight having no configuration for retention. The body portion 22 is adapted to be inserted into and reside substantially in the ureter 104. The distal end portion 30 has a predetermined configuration which advantageously serves several functions. The distal end portion 30 provides means for retaining the distal end portion 30 in the kidney 100. The distal end portion 30 is shaped to angled from the body portion 22 in such a way to facilitate safe placement and removal of the stent 10. The effect of the distal end portion 30 being angled from the body portion 22 of the stent 10 allows the distal end portion 30 to be partially uncoiled in the kidney 100 and for it to be removed without kinking or being pulled down intact into the ureter 104.

Figure 2:
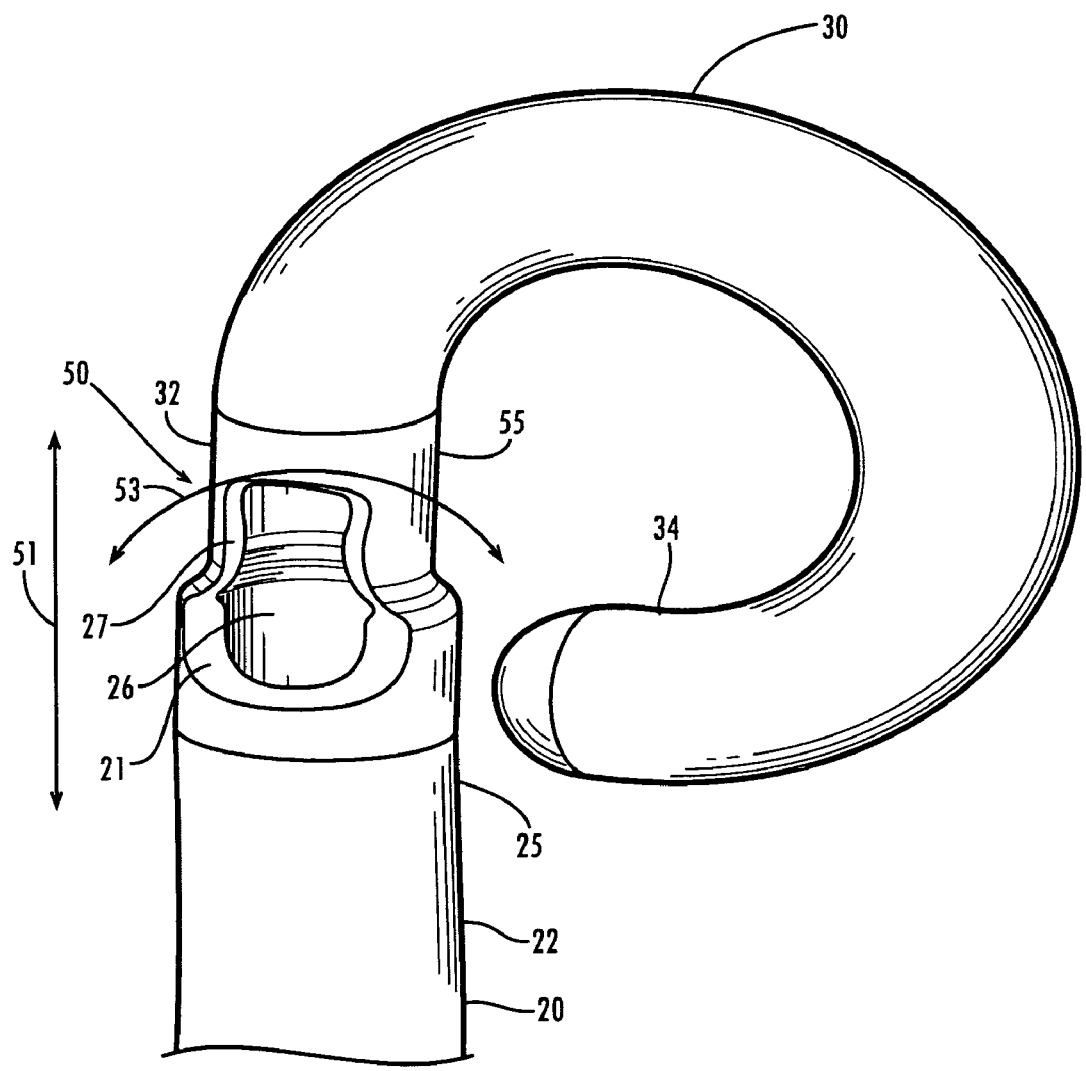
FIG. 2 is a partial cut-away view of a stent body portion and distal end portion in accordance with another embodiment of the present invention.

FIG. 2 is a partial cut-away view of the body portion 22 and distal end portion 30 in accordance with an embodiment of the present invention. The body portion 22 comprises an elongated tubular member 20 having a body portion wall 21 defining a lumen 26 therein. The body portion 22 further comprises a body portion distal end 25 and a body portion proximal end 23, as shown in FIG. 1.

The distal end portion 30 comprises a distal portion transition end 32 and a terminating end 34. The distal portion transition end 32 and the body portion distal end 25 are coupled by a distal transition region 50.

The distal transition region 50 is characterized by exhibiting a physical property that provides both longitudinal elasticity allowing for stretch and recoil, indicated by an axial arrow 51, as well as radial elasticity allowing for bending and recovery, indicated by a curving arrow 53.

In an embodiment in accordance with the present invention, the distal transition region 50 is characterized as a region having materials of differing material properties than either the body portion 22 and/or the distal end portion 30. The body portion 22 comprises a material having a less-compliant material property (harder) transitioning to a more compliant (softer) material. In production, this transition can be accomplished by, for example, a co-extrusion process where deposition of a first material is gradually ceased and deposition of a second is gradually increased.

In another embodiment in accordance with the present invention, the distal transition region 50 is characterized as a region of thinning of the wall 21 of the tubular member 20, wherein the tubular member 20 comprises a homogenous material. The body portion 22 comprises a wall 21 of a predetermined thickness and the transition region 50 comprises a wall 27 of a smaller predetermined thickness. In production, this effect can be accomplished by, for example, a co-extrusion process where deposition of a material is gradually reduced over the length of the transition region 50.

In another embodiment in accordance with the present invention, the distal transition region 50 is characterized as a region having a resilient coupling member 55 adapted to couple the body portion 22 with the distal end portion 30. The resilient coupling member 55 comprises a material of differing material properties than the body portion 22 and/or the distal end portion 30. The body portion 22 and distal end portion 30 comprises a material having a less compliant material property (harder), where in the resilient coupling member 55 comprises a more compliant (softer) elastic material.

In another embodiment in accordance with the present invention, in addition to having a distal transition region 50 as described above, the stent 10 further comprises a proximal transition region 56 (shown in FIG. 1) substantially the same as the distal transition region 50. The proximal transition region 56 couples the body portion 22 to the proximal end portion 40 and provides substantially the same properties as provided by the distal transition region 50.

The distal transition region 50 and the proximal transition region 56 provide the ability for the stent 10 to accommodate the dynamic urinary tract anatomy which stretches and relaxes. The relative push-and-pull of the kidney 100 and bladder 102 is accommodated for by the proximal transition region 50 and the distal transition region 56 by resiliently bending, stretching, and recovering with the respective movements of the anatomy. The accommodation provides increased patient comfort from contact irritation of the stent 10 within the anatomy. In addition, the accommodation reduces the potential for the distal end portion 30 or the proximal end portion 40 to migrate or dislodge from their respective locations.

The stent 10 may be formed from a variety of known materials which are biocompatible and have desired physical properties to be fabricated in the form hereafter described. An example of a suitable material is silicone, thermoplastic material, or elastomers or any material known to one skilled in the art.

Figure 3A:
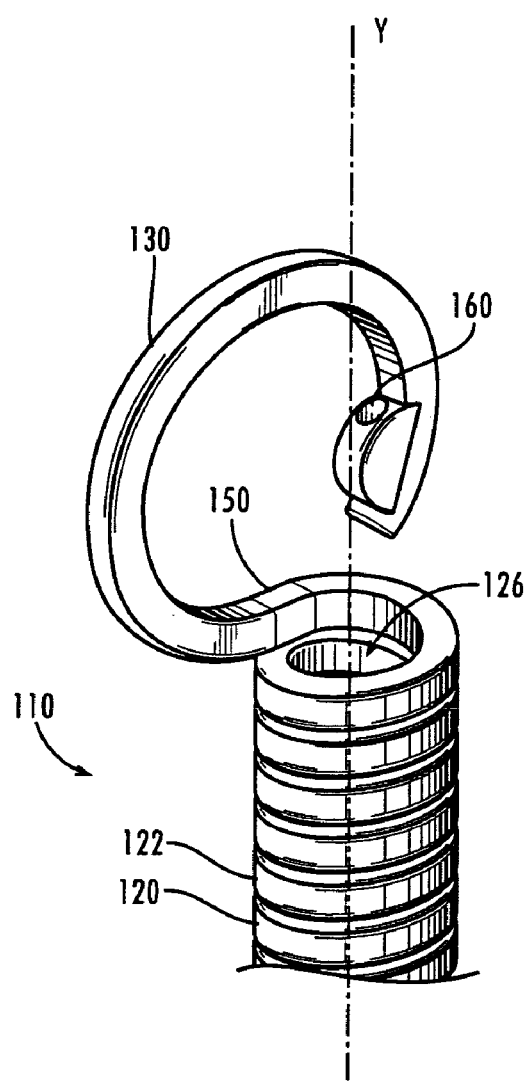
FIGS. 3A and 3B are perspective views of a stent body portion and distal end portion in accordance with another embodiment of the present invention.
Figure 3B:
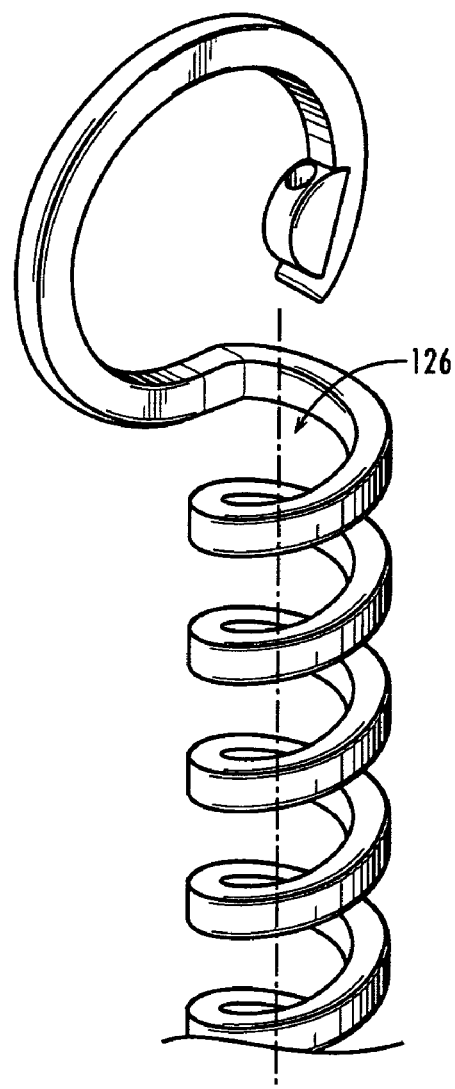
Figure 4:
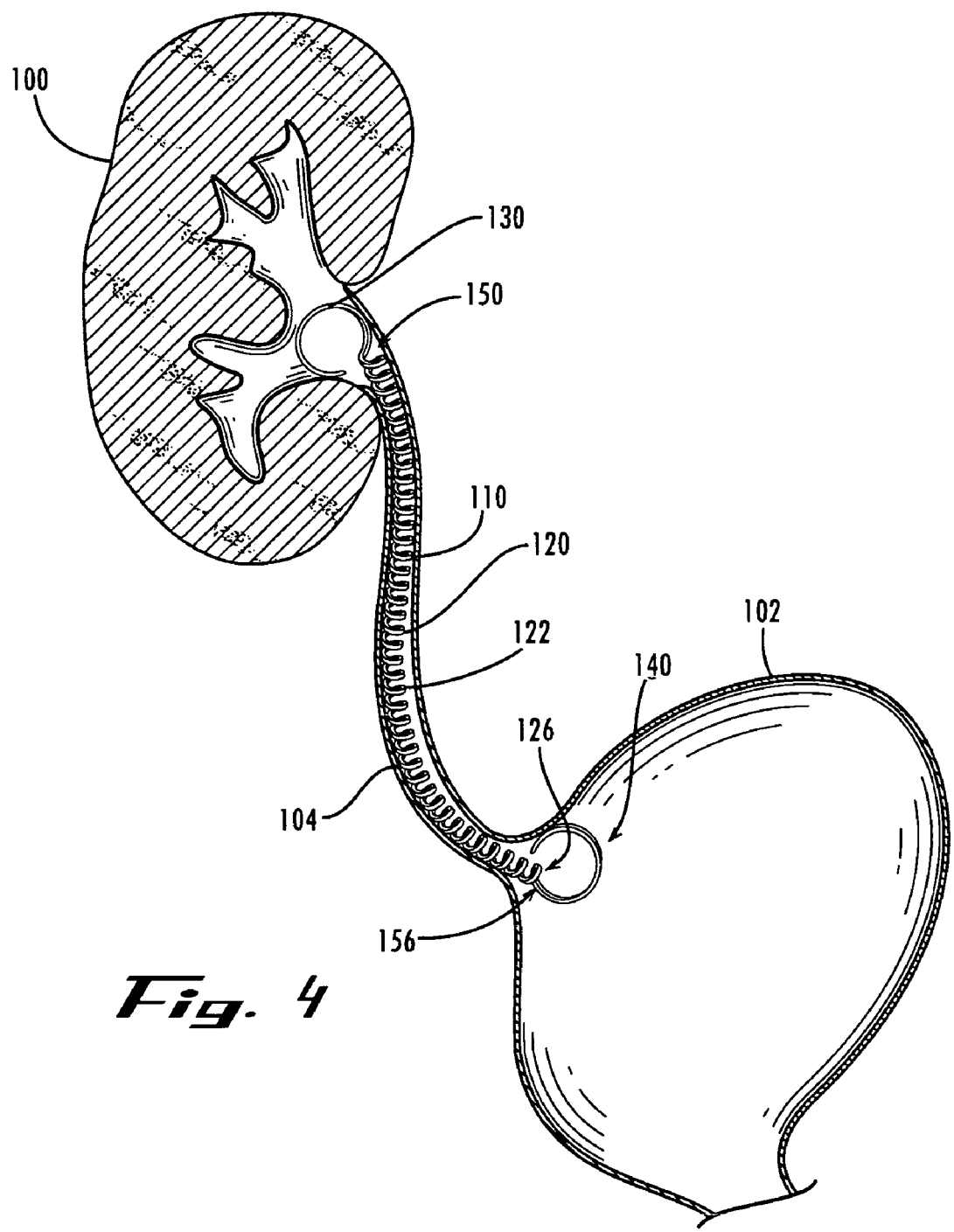
FIG. 4 is a front partial cross-sectional view of a ureteral stent within anatomy in accordance with another embodiment of the present invention.

FIGS. 3A and 3B are perspective views of a body portion 122 and distal end portion 130 of a stent 110 in accordance with an embodiment of the present invention. FIG. 4 is a partial cut-away view of the stent 110 as provided in anatomy, shown by way of example. The body portion 122 comprises an elongated member 120 formed into a helical coil having an axis Y defining a lumen 126 therein.

The elongated member 120 transitions to form the distal end portion 130 at a distal transition region 150. The distal transition region 150 is characterized by the transition of the coil configuration of the body portion 122 to a conventional curl configuration of the distal end portion 130.

In other embodiment, in similar arrangement, a proximal end portion 140 is provided in substantially the same configuration as the distal end portion 130, as shown in FIG. 4.

The stent 110 is fixed into the predetermined configuration, including, a helical coil for the body portion 122 and a kidney curl for the distal end portion 130, and, in some embodiments, a bladder curl for the proximal end portion 140, using any known suitable processes. In one embodiment, for example, the elongated member 120 comprises a polymer material capable of retaining a predetermined shape using heat-treatment techniques. The elongated member 120 is heated to a temperature exceeding the glass transition temperature of the polymer and shaped into a predetermined configuration. Necessarily, the polymer is selected so that the glass transition temperature of the polymer is higher than body temperature. In this way, a "memory" of the predetermined configuration is retained by the polymer. The stent 110, when implanted within the body, tends to return to the predetermined configuration when stretched or otherwise deformed from the predetermined configuration. The stent 110 can be subject to stretching or deformation, such as, during deployment or natural body movement.

In another embodiment in accordance with the present invention, the stent 110 is fixed into a predetermined configuration with the assistance of a structural member. The structural member is adapted to impart and resiliently retain a predetermined configuration to the elongated member 120. In one embodiment, the structural member comprises nickel-titanium alloy wire having a super-elastic, shape memory property. The structural member is coupled to the elongated member substantially along the length of the body portion 122. The structural member is adapted to retain a "memory" of the predetermined configuration. The stent 110, when implanted within the body, will tend to return to the predetermined configuration when stretched or otherwise deformed from the predetermined configuration.

Referring again to FIG. 4, the body portion 122 of the stent 110 is adapted to be positioned within the ureter. The lumen 126, formed by the coil of the body portion 122, provides fluid communication along its length from the distal end portion 130 to the proximal end portion 140.

The proximal end portion 140 is provided with retention means for retaining the proximal end portion 140 in the bladder 102. Alternatively, the proximal end portion 140 is substantially straight. If retention means are utilized, they may assume a variety of forms such as those commonly used in the art. For example, the proximal end portion 130 may include a J-shaped curve.

The stent 110 also includes a distal end portion 130 which includes retention means for retaining the distal end portion 130 in the kidney 100. The distal end portion 130 retention means comprises a distal end portion 130 being set in the shape in a variety of forms such as those commonly used in the art. The distal end portion 130 meets the body portion 122 of the stent 110 at a transition region 150. The placement of the stent 110 in a kidney 100 is shown in FIG. 4. The distal end portion 130 is placed in the renal cavity with the curl positioned away from the ureteropelvic junction. The curvature of the distal end portion 130 is adapted for retention of the distal end portion 130 in the kidney 100. The configuration of the distal end portion 130 of the stent 110 permits easy placement of the distal end portion 130 in the renal pelvis.

Once a physician has selected a stent 110 for use in the patient, after considering the normal size of the ureteral passage and the length of the ureter 104, the placement of the ureteral stent 110 may by accomplished in accordance with known prior art techniques. A wire stylet, or guidewire, not shown, which can be formed of stainless steel wire, is inserted into the lumen 126 at the proximal end portion 140 of the stent 110.

In accordance with an embodiment of the present invention, the distal end portion 130 further comprises a guidewire-coupling fixture 160 (as shown in FIGS. 3A and 3B). The guidewire-coupling fixture 160 provides a means for accepting an end of the guidewire so as to provide a means for pushing the distal end portion 130 into the anatomy. The guidewire is inserted into the lumen 126 at the proximal end portion 140 and advanced to the distal end portion 130. The guidewire is coupled to the guidewire-coupling fixture 160 providing a means for the guidewire to push the distal end portion 130 through the bladder 102, into the ureter 104, and into the kidney 100. In one embodiment, pushing the guidewire tends to straighten out the helical coil of the body portion 120, reducing the profile of the body portion 120 to assist in the insertion.

Confirmation that the renal pelvis has been entered by the stent 110 can be obtained by x-ray. If desired, radiopaque measurement markings or other suitable radiopaque indicia can be incorporated on the stent 110 and are visible during x-ray examination to aid in confirming the position of the stent 110.

After the stent 110 has been inserted into a predetermined distance into the renal pelvis, the guidewire is withdrawn, enabling the curl to form in the distal end portion 130 and enabling the helical coil of the body portion 122 to recoil. The distal end portion 130 bears against the walls of the renal pelvis and the body portion 122 against the ureter 104.

Alternatively, the ureteral stent 110 may be placed in the ureter during surgery. Other modes of inserting and/or straightening a device also known in the art.

Dimensions for the body portion 120 of the ureteral stent 110 of the present invention are not critical; however, they include internal diameters of 4.5 to 8.5 French, and lengths ranging from 20 cm. to 32 cm.

The elongated member 120 according to the invention may, be constructed from any of a number of materials. Materials that are useful include, for example, materials that are able to flex but also retain their shape, to a degree, when they are perturbed. Additionally, useful materials are, for example, materials that have a resilient quality, being able to regain at least some of their original shape when the stent 110 ceases to be perturbed and/or resist, for example, compression. One such material that combines these features is Percuflex™. Moreover, thermo-formable materials, including, for example, Percuflex™ are useful in the practice of the invention.

Concerns mentioned above with respect to stents also apply in the catheter and intubation arts, which include, without limitation: intravenous catheters, guiding catheters, sheaths, umbilical catheters, trocar catheters, heart catheters (including, valvostomy catheters, angioplasty catheters, arthroscopy catheters, and the like), perfusion catheters, suction catheters, oxygen catheters, endoscopy catheters, endotracheal tubes, stomach tubes, feeding tubes, lavage tubes, rectal tubes, urological tubes, irrigation tubes, aneurysm shunts, stenosis dialators, trocars, and inserters, generally.

While the invention has been described in connection with specific embodiments thereof, it will be understood that it is capable of further modification. This application is intended to cover any variations, uses, or adaptations of the invention following, the general principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A stent comprising:
    an elongated tubular member having a body portion, a proximate end portion, and a distal end portion, the tubular member having an axial lumen therein adapted to provide fluid communication from the distal end portion to the proximal end portion, the tubular member further comprising a resilient distal transition region coupling the distal end portion to the body portion;
    the distal transition region comprising a resiliently compliant material that provides a gradual transition of material properties from the body portion across to the distal end portion, the properties imparting to the distal transition region resilient bending, stretch/recoil, and radial compressibility in situ; and
    the distal end portion comprises a curl having an angle sufficient to retain the distal end portion against the walls of a body structure and having a first, coiled state when in its intended place in a body structure and a second uncoiled state when the curl is inserted or withdrawn through a relatively narrow lumen leading to the body structure.

2. The stent of claim 1, wherein the tubular member further comprises:
    a resilient proximal transition region coupling the proximal end portion to the body portion.

3. The stent of claim 1, wherein the resilient distal transition region is characterized as a region comprising a more compliant material than that comprising the body portion and/or the distal end portion.

4. The stent of claim 1, wherein the body portion comprises a wall having a first wall thickness, the resilient distal transition region having a wall with a second wall thickness less than the first wall thickness.

5. The stent of claim 1, wherein the resilient distal transition region comprises a resilient coupling member adapted to couple the body portion to the distal end portion.

6. A ureteral stent for maintaining drainage between a kidney and a bladder comprising:
    an elongated tubular member having a body portion, a proximate end portion, and a distal end portion, the tubular member having an axial lumen therein adapted to provide fluid communication from the distal end portion to the proximal end portion, the tubular member further comprising a resilient distal transition region coupling the distal end portion to the body portion, the proximal end portion adapted for placement in the bladder, the distal end portion including retention means adapted for retaining the distal end portion in the kidney;
    the distal transition region comprising a resiliently compliant material that provides a gradual transition of material properties from the body portion across to the distal end portion, the properties imparting to the distal transition region resilient bending, stretch/recoil, and radial compressibility in situ;
    the distal end portion comprises a curl having an angle sufficient to retain the distal end portion against the walls of the kidney and having a first, coiled state when in the kidney and a second uncoiled state when the curl is inserted or withdrawn through the ureter leading to the kidney.

7. The stent of claim 6, wherein the resilient distal transition region is characterized as a region comprising a more compliant material than that comprising the body portion and/or the distal end portion.

8. The stent of claim 6, wherein the body portion comprises a wall having a first wall thickness, the resilient distal transition region having a wall with a second wall thickness less than the first wall thickness.

9. The stent of claim 6, wherein the resilient distal transition region comprises a resilient coupling member adapted to couple the body portion to the distal end portion.

10. A ureteral stent for maintaining drainage between a kidney and a bladder comprising:
    an elongated tubular member having a body portion, a proximate end portion, and a distal end portion, the tubular member having an axial lumen therein adapted to provide fluid communication from the distal end portion to the proximal end portion, the tubular member further comprising a resilient distal transition region coupling the distal end portion to the body portion, the proximal end portion adapted for placement in the bladder, the distal end portion including retention means adapted for retaining the distal end portion in the kidney;
    wherein the distal transition region comprises a resiliently compliant material that provides a gradual transition of material properties from the body portion across to the distal end portion, the properties imparting to the distal transition region resilient bending, stretch/recoil, and radial compressibility in situ; and
    the distal end portion comprises a curl having an angle sufficient to retain the distal end portion against the walls of the kidney and having a first, coiled state when in the kidney and a second uncoiled state when the curl is inserted or withdrawn through the ureter leading to the kidney.

* * * * *